(12) United States Patent
Oshiro et al.

(10) Patent No.: US 8,333,933 B2
(45) Date of Patent: Dec. 18, 2012

(54) PROCESS CHALLENGE DEVICE FOR A HIGH-PRESSURE STEAM STERILIZER AND SHEET FOR A CHALLENGE DEVICE

(75) Inventors: Seisaku Oshiro, Osaka (JP); Toshiki Fujisawa, Osaka (JP)

(73) Assignee: Sakura Color Products Corporation (JP)

( * ) Notice: Subject to any disclaimer, the term of this patent is extended or adjusted under 35 U.S.C. 154(b) by 1261 days.

(21) Appl. No.: 11/799,415

(22) Filed: May 1, 2007

(65) Prior Publication Data

US 2007/0264683 A1    Nov. 15, 2007

(30) Foreign Application Priority Data

May 10, 2006    (JP) ................................ 2006-131707

(51) Int. Cl.
  *B01L 3/00*    (2006.01)
  *G01N 31/22*   (2006.01)
  *G01N 31/00*   (2006.01)
(52) U.S. Cl. ........................ 422/430; 422/401
(58) Field of Classification Search .................. 422/58, 422/60, 401, 430; 436/1
  See application file for complete search history.

(56) References Cited

U.S. PATENT DOCUMENTS

| | | | | |
|---|---|---|---|---|
| 4,486,387 A | * | 12/1984 | Augurt | 422/58 |
| 5,281,400 A | * | 1/1994 | Berry, Jr. | 422/295 |
| 5,435,971 A | * | 7/1995 | Dyckman | 422/61 |
| 2007/0095699 A1 | * | 5/2007 | Frieze et al. | 206/438 |

FOREIGN PATENT DOCUMENTS

| | | |
|---|---|---|
| JP | 61-134991 | 8/1986 |
| JP | 62-64365 | 3/1987 |
| JP | 01-166759 | 6/1989 |
| JP | 02-019160 | 1/1990 |
| JP | 02026557 A * | 1/1990 |
| JP | 04-336069 | 11/1992 |
| JP | 08-282147 | 10/1996 |
| JP | 10-209640 | 8/1998 |
| JP | 2002-367662 | 12/2002 |

* cited by examiner

*Primary Examiner* — Kevin Joyner
(74) *Attorney, Agent, or Firm* — Wood, Phillips, Katz, Clark & Mortimer

(57) ABSTRACT

An object of the present invention is to provide a process challenge device for a high-pressure steam sterilizer capable of reuse with little trouble.

A process challenge device 1 for a high-pressure steam sterilizer, includes a plurality of stacked steam permeable bodies 7, 8, and 9 formed by a material capable of permeating of steam 11 and an indicator 10. The steam permeable bodies 8 (except the steam permeable bodies 7 and 9 arranged at both sides among the stacked steam permeable bodies 7, 8, and 9) each have an opening 8a for accommodating the indicator 10. The steam permeable bodies 7, 8, and 9 are stacked, so that the indicator 10 is surrounded by the inner wall of a cavity 24 formed by the openings 8a of the intermediate steam permeable bodies communicated with one another and the steam permeable bodies 7 and 9 arranged at both sides. The indicator 10 is contained in the cavity 24, so that a group 6 of the above-mentioned stacked steam permeable bodies containing the indicator 10 therein is fitted into and taken out of a casing 2 at will.

40 Claims, 11 Drawing Sheets

PROCESS CHALLENGE DEVICE FOR A HIGH-PRESSURE STEAM STERILIZER AND SHEET FOR A CHALLENGE DEVICE

BACKGROUND OF THE INVENTION

1. Field of the Invention

The present invention relates to high-pressure steam sterilizers for sterilizing clothes or instruments for use in medical purposes.

2. Description of the Related Art

Conventionally, autoclaves are generally used for sterilizing articles such as clothes or instruments for use in medical purposes due to its low cost for introduction and availability of water that is harmless to humans. Autoclaves sterilize medical instruments by a process of steaming under high pressure. Specifically, autoclaves contains in its chamber articles to be sterilized, removing air in the chamber by a vacuum pump, then supplying high-pressure steam, so as to sterilize the articles.

If and when steam permeates poorly (insufficiently) into articles to be sterilized, desired sterilization effect is not achieved. Thus, tests by a process challenge device (PCD) have been conventionally performed, so as to determine whether steam has permeated well or not into articles to be sterilized with monitoring an indicator.

A test by the PCD is carried out by providing an indicator for showing some reaction on exposure to steam and a steam permeable body for giving a predetermined resistance to steam flowing therethrough, then passing steam through the steam permeable body to the indicator, and determining an amount of steam that has reached the indicator based on reaction degree of the indicator so as to measure an sterilization effect. The test is carried out in daily sterilization. The steam permeable body to be used generally meets the AAMI (Association for Advancement of Medical Instrumentation) standard in the United States and is made in the following way. Surgical towels are cut into predetermined dimensions, further folded in a predetermined way, and used with stacked in 16 pieces. An indicator is interposed between the seventh and eighth pieces. The entire 16 pieces of towels including therein the indictor are secured with tape, forming steam permeation resistance (steam permeable body) to the indicator. The towels having been used are washed, dried, and then reused.

The test performed by the AAMI standard requires such complicated preparations as described above, and further requires the need and time to wash and dry the towels for reuse thereof. There is another test called the Bowie & Dick test different from the test performed by the AAMI standard in sterilization. The Bowie & Dick test is different from the test performed by the AAMI standard in its specification, but the purpose of determination of a sterile condition is common to the both. An indicator for simplifying a test equivalent to the Bowie & Dick test is disclosed, for example, in the patent document 1.

Patent Document 1: Japanese Patent No. 3130557

SUMMARY OF THE INVENTION

Problem to be Solved by the Invention

The patent document 1 discloses "an indicator pack" composed of stacked materials wrapped up by an outer covering. The stacked materials include an indicator sheet colored by existence of heating steam. The outer covering has small holes so as to pass steam therethrough. The outer covering is torn to take out the indicator sheet after sterilization.

The configuration disclosed in the patent document 1 is such a disposal type as to inevitably tear the outer covering for carrying out a test, rendering nonreusable. Further, there is no choice but to use an indicator preliminarily contained in an outer covering, resulting in no selection of an indicator wished for by users (those who are to perform examinations).

An object of the present invention made in view of the problems and drawbacks in the art described above is therefore to provide a process challenge device for a high-pressure steam sterilizer reusable with little trouble.

Means to Solve the Problem

An aspect of the present invention is a process challenge device for a high-pressure steam sterilizer, including a plurality of steam permeable bodies formed by a steam permeable material, an indicator changeable in appearance on exposure to a predetermined temperature history, and a holder, wherein the steam permeable bodies include at least one end steam permeable body and a plurality of intermediate steam permeable bodies, wherein the steam permeable bodies are stacked with the end steam permeable body arranged at at least one end, the intermediate steam permeable bodies each having an opening, the openings of the intermediate steam permeable bodies being communicated with one another to form a cavity, the cavity being closed at at least one end by the end steam permeable body, the indicator being contained in the cavity, and wherein the holder holds the stacked steam permeable bodies having therein the indicator in a stacked fashion.

The indicator changes in appearance (changes color, for example) on exposure to a predetermined temperature history corresponding to completion of sterilization. The holder is designed to hold the steam permeable bodies in a stacked fashion and release the holding of the bodies. Herein, in the case of one end steam permeable body, the other end can be closed by a plate.

According to the present aspect, stacking of the intermediate steam permeable bodies allows the openings to be communicated with one another, so as to form the cavity, which is surrounded by the inner walls of the openings and the end steam permeable body. The indicator is contained in this cavity. Consequently, in sterilization by steam, the steam permeates moderately into the steam permeable bodies and reaches the indicator within the cavity.

After sterilization by steam, release of the holding of the bodies by the holder allows the indicator to be taken out without damaging components such as the steam permeable bodies. Consequently, the components are reusable with little trouble. Further, as long as being accommodated in the cavity, an indicator can be employed at user's discretion each time.

Preferably, the steam permeable bodies each are of a shape of a sheet. The shape of a sheet is easy to be stacked.

In the present aspect, preferably, the steam permeable bodies all have the same outer shape. That facilitates stacking thereof. However, only the intermediate steam permeable bodies may have the same outer shape.

Preferably, the intermediate steam permeable bodies each have a positioner, whereby a direction of the intermediate steam permeable bodies is adjusted or aligned in being stacked. It is also possible to provide a similar positioner in the end steam permeable body. The positioner is formed in such a simple structure as providing with a cutoff portion or coloring at a side to be aligned.

Provision of the positioner for aligning the direction of the steam permeable bodies to be stacked thereto readily orients the direction of the openings in the same direction, thereby facilitating assembly of the process challenge device.

The steam permeable bodies are readily fitted into the casing or bound by a binder by aligning the directions of the bodies.

Preferably, the steam permeable bodies have at least two end steam permeable bodies, so as to be stacked with the end steam permeable bodies arranged at both ends thereof, the cavity being closed at both sides by the end steam permeable bodies. An arrangement of the end permeable bodies at both ends facilitates formation of the process challenge device. It is the most simple to arrange two end steam permeable bodies at both ends.

It is preferable that the holder is a casing and that the stacked steam permeable bodies are set into the casing, so as to be held in a stacked fashion. That facilitates holding of the bodies in a stacked fashion with a simple configuration. Further, reuse is easy.

Preferably, the casing has holes for passing steam therethrough, through which the steam is introduced into the casing to reach the steam permeable bodies set in the casing. The casing is preferably made of a steam-impermeable or a low steam permeable material. According to this configuration, sterilization tests by steam are readily carried out with the steam permeable bodies contained in the casing.

Preferably, the holes have a total area of 3 to 30% of the overall area of a surface where the holes are formed, in order to obtain an appropriate amount of high-pressure steam passing therethrough.

It is preferable that the casing includes a main body and a lid and is lockable with the lid closed. This configuration achieves holding of the steam permeable bodies more certainly.

The holder may be a binder such as a string, a tape, or a rubber band, and the stacked steam permeable bodies may be bound by the binder, so as to be held in a stacked fashion. That achieves easy reuse with a simple configuration.

The indicator may be appropriately selected from the conventional ones. Specifically, it is suitable to be selected from a group consisting of a chemical indicator, a biological indicator and a data logger indicator. A data logger indicator is designed to send data detected by a detector such as a temperature sensor to a data processor such as a computer, whereby the data is analyzed.

It is possible to test using a discretional combination of a plurality of indicators or a plurality kind of indicators.

Another aspect of the present invention is a process challenge device for a high-pressure steam sterilizer, including a plurality of steam permeable bodies formed by a steam permeable material and a holder, wherein the steam permeable bodies include at least one end steam permeable body and a plurality of intermediate steam permeable bodies, the intermediate steam permeable bodies each having an opening, the openings of the intermediate steam permeable bodies being adapted to be communicated with one another by stacking of the steam permeable bodies with the end steam permeable body arranged at the end, so as to form a cavity closed at at least one end by the end steam permeable body, the cavity being designed to contain an indicator changeable in appearance on exposure to a predetermined temperature history, and wherein the holder is adapted to hold the stacked steam permeable bodies in a stacked fashion.

The present aspect is a set of a plurality of steam permeable bodies and a holder for manufacturing the process challenge device of the foregoing aspect.

The process challenge device of the foregoing aspect is manufactured by assembling of these components further with an indicator to be contained in the cavity.

Preferably, the indicator is one selected from a group consisting of a chemical indicator, a biological indicator and a data logger indicator.

Preferably, the steam permeable bodies each are of a shape of a sheet. The shape of a sheet is easy to be stacked.

In the present aspect, preferably, the steam permeable bodies all have the same outer shape. That facilitates stacking thereof. However, only the intermediate steam permeable bodies may have the same outer shape.

Preferably, the steam permeable bodies each have a positioner for adjusting or aligning their directions.

The positioner is formed in such a simple structure as providing with a cutoff portion or coloring at a side to be aligned.

It is preferable that the steam permeable bodies have at least two end steam permeable bodies, the openings being adapted to be communicated with one another by stacking of the steam permeable bodies with the end steam permeable bodies arranged at both ends thereof, so as to form the cavity closed at both sides by the end steam permeable bodies. An arrangement of the end permeable bodies at both ends facilitates formation of the process challenge device. It is the most simple to arrange two end steam permeable bodies at both ends.

The steam permeable bodies may be stacked and fixed to one another at one side. According to such a structure, it is easy to hold relative position of the stacked steam permeable bodies.

Still another aspect of the present invention is a process challenge device for a high-pressure steam sterilizer, including a plurality of steam permeable bodies formed by a steam permeable material and a holder, wherein the steam permeable bodies include at least one end steam permeable body and a plurality of intermediate steam permeable bodies, the intermediate steam permeable bodies each having a removable portion, so as to form an opening by removing the portion, the openings of the intermediate steam permeable bodies being adapted to be communicated with one another by stacking of the intermediate steam permeable bodies in which the openings are formed and the end steam permeable body arranged at the end, so as to form a cavity closed at its end by the end steam permeable bodies, the cavity being designed to contain an indicator changeable in appearance on exposure to a predetermined temperature history, and wherein the holder is adapted to hold the stacked steam permeable bodies in a stacked fashion.

The present aspect is also a set of a plurality of steam permeable bodies and a holder for manufacturing the process challenge device of the most foregoing aspect. However, in the present aspect, the intermediate steam permeable bodies each have the removable portion. Thus, for forming the openings, it is only necessary to remove the portion according to need. The removable portion can be provided by formation of a breakable line so as to surround the portion. The breakable line can be formed by provision of broken portions in dashed line fashion, for example, or provision of a portion to be readily broken (thin wall portion, for example) in the form of a line.

By stacking of the intermediate steam permeable bodies having a desired area, shape, and number of openings, a cavity suitable for accommodating an indicator to be used of a size, kind, or number is formed. Further, the number of the intermediate steam permeable bodies having the openings may be set depending on the thickness of the indicator to be used. Except the removable portion, a preferred embodiment in the present aspect is similar to the aspect previously described, unless otherwise stated.

As to the end steam permeable body, the use of one having the shape identical with the intermediate steam permeable bodies without removing the removable portion makes its structure simple. However, it is not necessary to have the shape identical with the intermediate steam permeable bodies.

The removable portion is formed in advance depending on an indicator to be contained. The breakable line (viz. a shape of the openings after breaking) can be formed at discretion into a shape such as a circle, an elongated hole, a square, or a triangle. The number of the removable portion(s) provided in the steam permeable bodies is also set at discretion. Further, the removable portion can be composed of a plurality of blocks as well as in aspects described below. That is, the number of a portion to be removed so as to form the cavity for accommodating the indicator can be set at discretion.

Yet another aspect of the present invention is a sheet for a challenge device, being made of a steam permeable material, and including a removable portion so as to form at least one opening thereon by removal of the portion, wherein the portion is composed of a plurality of blocks, so as to form a desired area, shape, and number of openings by removal of at least one of the discretional number of blocks.

The present aspect relates to an individual sheet for a challenge device capable of being the above-mentioned steam permeable body. The cavity depending on a size, kind, and number of an indicator to be used is formed by stacking of a plurality of sheets having a desired area, shape, and number of openings.

Yet still another aspect of the present invention is a sheet for a challenge device, being made of a steam permeable material, including a removable portion so as to form an opening thereon by removal of the portion, a breakable line surrounding an entire area of the portion, and a breakable line adapted to divide the portion into a plurality of blocks.

The present aspect also makes it possible to form the cavity depending on an indicator to be used by stacking of a plurality of sheets having a desired area, shape, and number of openings.

In the present aspect, the sheet preferably includes a positioner, whereby a direction of a plurality of sheets is adjusted or aligned in being stacked. The positioner is formed in such a simple structure as providing with a cutoff portion or coloring at a side to be aligned.

In the aspects of the present invention, the steam permeable material for the steam permeable body or the sheet is one selected from a group consisting of paper and pulp.

The steam permeable body or the sheet is made of paper or pulp, so that multiple reuses are achieved. Further, the steam permeable body is manufactured inexpensively. Still further, employment of paper or pulp thinner than towel conventionally used can provide miniaturization of the entire device.

DESCRIPTION OF THE PREFERRED EMBODIMENT

Now, an embodiment of the present invention will be described below in detail, making reference to the accompanying drawings.

FIGS. 1 to 4 each are a perspective view of a process challenge device for a high-pressure steam sterilization 1 (hereinafter referred to as a challenge device 1) embodying the present invention, showing from a disassembled state to an assembled state in the order of FIG. 1 to FIG. 4. First, configurations of the challenge device 1 will be described below, making reference to FIGS. 1 to 4, and then, the features of each configuration will be described.

Figure 1:
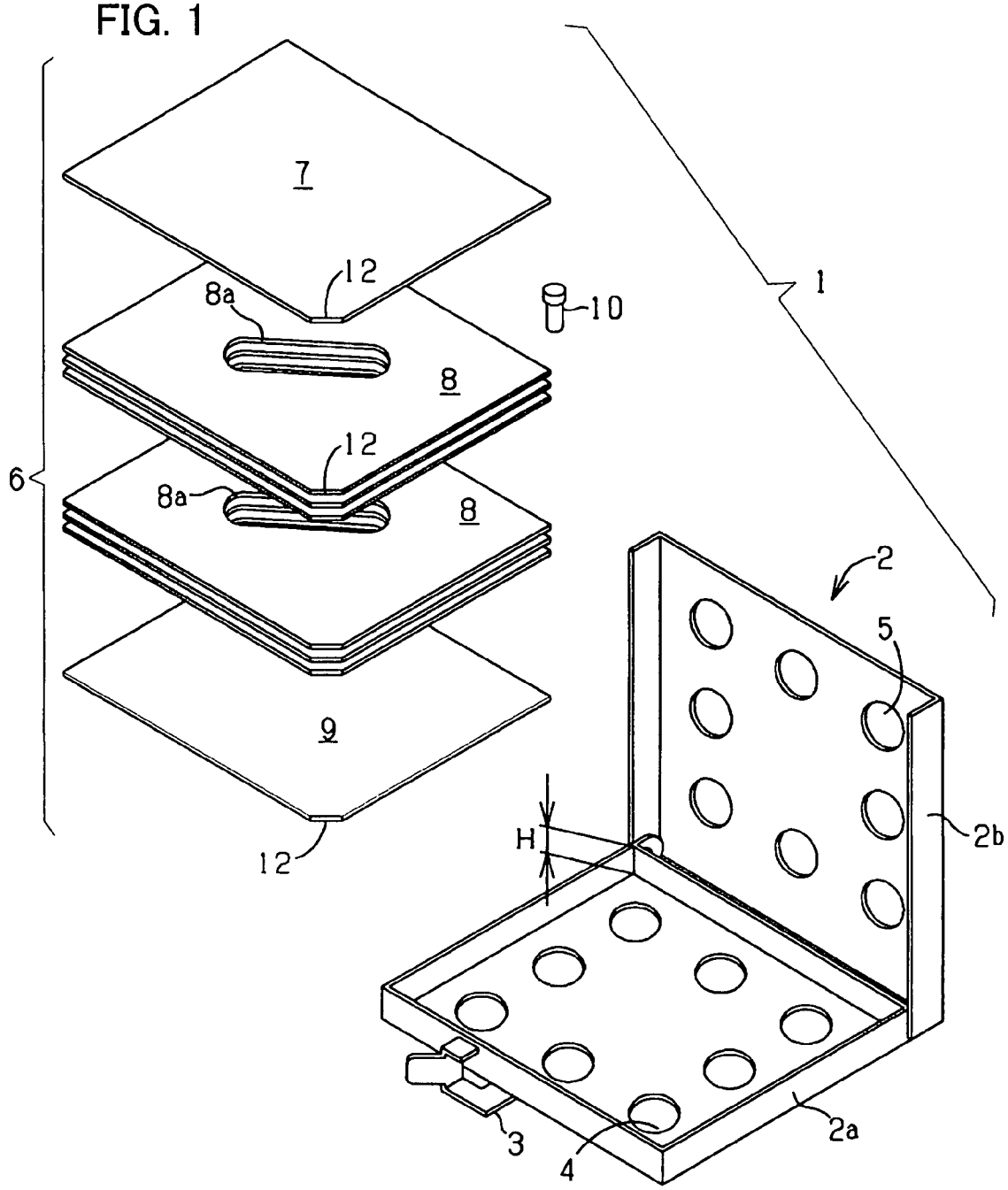
FIG. 1 is an exploded perspective view of a challenge device for a high-pressure steam sterilizer embodying the present invention.
Figure 4:
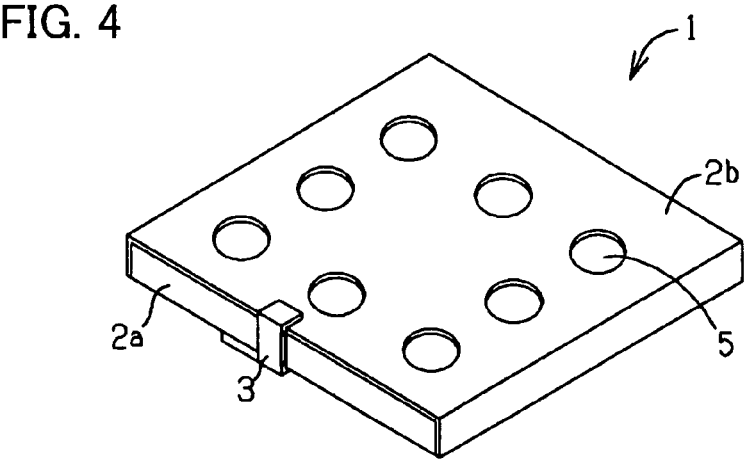
FIG. 4 is a perspective view of the challenge device in a state in which a lid of the casing is closed.

Referring to FIG. 1, the challenge device 1 of the present invention mainly consists of a casing (holder) 2, a group of sheets (steam permeable bodies) 6, and an indicator 10. The casing 2 has a main body 2*a* and a lid 2*b*, the lid 2*b* being openable and closable relative to the main body 2*a* by a hinge mechanism. The main body 2*a* is provided with a latch 3, which secures the lid 2*b* to the main body 2*a* when the lid 2*a* is closed. Specifically, as shown in FIG. 4, the latch 3 is secured rotatably to the main body 2*a* by a shaft (not shown), so that the lid 2*b* is secured unrotatably to the main body 2*a by being closed and locked with the latch 3.

The lid 2*b* may be secured to the main body 2*a* by a screw mechanism, instead of the latch 3. The lid 2*b* needs not necessarily to be rotatably to the main body 2*a* by a hinge, and may employ another structure. For example, it is possible to employ an engagement mechanism or such a matchbox mechanism that the lid 2*b* is provided with guide rails, along which the main body 2*a* is slid to be accommodated into the lid 2*b*. Further, a plurality of screws may removably fix the periphery of the lid 2b to the main body 2a. Further, the lid 2b may be clamped the main body 2a.

Among the above-mentioned configurations, it is especially preferable to connect the lid 2b and the main body 2a openably and closably by a hinge mechanism and fix them with at least one fixture such as the latch 3.

The lid 2b has a plurality (eight in the example in FIGS. 1 to 4) of discrete lid holes 5 strategically located so as to pass therethrough steam 11 (FIG. 6) as described below. The number of the holes 5 to be formed or a layout thereof may be arranged at discretion in view of an environment in a sterilizing room (or autoclaves) not shown.

The main body 2a also has discrete, strategically located, main body holes 4. The main body holes 4 are situated at the location substantially corresponding to that of the lid holes 5 in plan view when the lid 2b is closed. The main body 2a and the lid 2b each are made of a high-pressure steam resistant material such as stainless steel (such as SUS 304 specified by JIS), aluminum, copper, titanium, various types of alloy thereof, a molding resin such as polyester, nylon, Teflon (registered trademark of polytetrafluoroethylene), polycarbonate, polyethylene, or polypropylene, ceramics such as glass, borosilicate glass, Pyrex (registered trademark of borosilicate glass), alumina or zirconia, glass lining, or enamel. In particular, stainless steel (SU304) is the most preferable.

The main body holes 4 and the lid holes 5 each are of a circular shape in the example shown in FIG. 1, but may be selected at discretion from a group consisting of a geometrical form such as a square, a triangle, a star shape, an oval, a slot-like shape, a lattice-like shape, a mesh-like shape, a cross, or a spiral shape, various kinds of language characters, a common mark, a traditional design from any cultural zone, and an amorphous shape without any particular meaning or any rule. In particular, a circular shape is the most preferable. The positions of the main body holes 4 and the lid holes 5 substantially correspond to each other in plan view, but may not necessarily do.

The total area of the main body holes 4 is arranged in the range of about 3 to 30% of the entire area of the surface of the main body 2a where the main holes 4 are formed. The same can be said for the lid holes 5. Herein, the above-mentioned percentage is preferably in the range of 5 to 20%, and more preferably, in the range of 8 to 12%. Such an arrangement of the areas of the main body holes 4 and the lid holes 5 in this way ensures an appropriate amount of high-pressure steam passing therethrough.

Now, the group 6 of sheets will be described in detail below.

Referring to FIG. 1, the group 6 of sheets is constituted by an upper sheet (end steam permeating body) 7, a plurality of intermediate sheets (intermediate steam permeating bodies) 8, and a lower sheet (end steam permeating body) 9. The example shown in FIG. 1 has one upper sheet 7, 16 intermediate sheets 8 (only six sheets of them illustrated in FIG. 1), and one lower sheet 9. Herein, the number of the upper sheet 7 and the lower sheet 9 each may be more than one. The combined thicknesses of the upper and lower sheets(s) 7,8 are substantially the same. Among the stacked group 6 of sheets, the intermediate sheets 8 arranged between the upper and the lower sheets 7 and 9 each have an opening 8a, which openings collectively define a cavity. The holes 4, 5 are spaced at substantially like intervals, each from adjacent holes 4, 5, around the cavity defined by the openings 8a. As shown, the holes 4, 5 surround the cavity defined by the openings 8a.

Each of the sheets is not necessarily made of a single material, but would be better selected from materials available inexpensively such as paper or pulp and further resistant to the frequent exposure to high-pressure steam. A material of 100% pulp, for example, withstands about 20 to 30 runs of examination. Employment of paper or pulp, which is thinner than towel used in the art, as a material of the group 6 miniaturizes a casing for accommodation, thereby miniaturizing the entire device.

Each of the sheets is also made of a material steam-permeable, easy to be manufactured and molded, and undeteriorated under an operating condition (environmental condition) for sterilization by high-pressure steam. Cotton or glass fiber compressed in a unified manner, heat-resisting nonwoven fabric, paper, cork, or pulp can be employed, for example. In particular, a material of 100% pulp is the most preferable.

The example shown in FIG. 1 has one upper sheet 7, a top surface of the sheet 7 being opposed to (or contacting with) the back of the lid 2b, and a bottom surface thereof contacting with a top surface of a sheet placed at the top of the intermediate sheets 8.

Similarly, the example has one lower sheet 9, a bottom surface of the sheet 9 being placed on the main body 2a, and a top surface of the sheet 9 contacting with a bottom surface of a sheet placed at the bottom of the intermediate sheets 8.

The example has 16 intermediate sheets 8 (only six sheets of them illustrated in FIG. 1), each of which has the opening 8a extending diagonally, as shown in FIG. 1. The openings 8a of the intermediate sheets 8 each are located at the same position in plan view. The more the intermediate sheets 8 increase in number, the more a cavity 24 formed by the openings 8a communicated with one another deepens. The indicator 10 is contained in the cavity 24. The number of the intermediate sheets 8 is arranged such that the cavity 24 is so deep as to accommodate the indicator 10. At least one upper sheet 7 and at least one lower sheet 9 are arranged so as to close the top opening and the bottom opening of the cavity 24.

The remaining usable times of each sheet are readily figured out by printing or describing a condition such as the number of the use of each sheet (the number of test runs). High-pressure steam-proof inks are to be used in order to print or describe with a pen a condition such as the number. In embodying the present invention, the experiments reveal that each sheet is sufficiently resistible to the uses of 25 times or more. Specifically, sufficient sterilization effect is achieved in the $25^{th}$ use.

The opening 8a is an elongated hole extending diagonally in the example shown in FIG. 1, but may have a shape selected at discretion from other shapes such as a circle, a square, a triangle, and an oval. In particular, an elongated hole or a circle is the most preferable. Further, only if the indicator 10 is accommodated in the cavity 24 formed by the openings 8a communicated with one another, it is not necessary to make the shapes of the openings 8a of the stacked intermediate sheets 8 identical with one another. Specifically, even if the intermediate sheets 8 having the openings 8a of, for example, a circular, a rectangular, and a triangular shape are stacked, irregular shapes or relative displacements in plan view of the openings 8a have no difficulty only if the indicator 10 is accommodated in the cavity 24.

Figure 5:
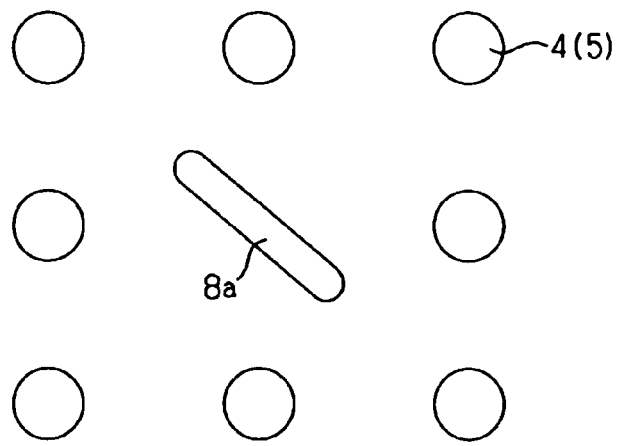
FIG. 5 is a plan view showing a layout of main body holes or lid holes formed on the casing and an opening of intermediate sheets.

However, as shown in FIG. 1, in the case that the main body holes 4 and the lid holes 5 formed on the casing 2 are arranged alongside (or parallel to) the periphery of a square shape of the casing 2 in plan view, the openings 8a of the intermediate sheets 8, as shown in FIG. 5, are preferably elongated holes extending diagonally to the square. In other word, it is preferable to make an arrangement so that the high-pressure steam 11 described below reach the openings 8a (viz. indicator 10) with substantially equivalent resistance through either hole (the main body holes 4 or the lid holes 5) through which the steam 11 is introduced. The example shown in FIG. 1 has the openings 8*a* each in the form of an elongated hole, thereby substantially equalizing the distances of the openings 8*a* to the main body holes 4 and the lid holes 5, so that the steam 11 reaches the openings 8*a* with substantially equivalent resistance through either of the main body holes 4 and the lid holes 5.

Herein, FIG. 5 is a plan view showing a layout of the main body holes 4 or the lid holes 5 formed on the casing 2 and the openings 8*a* of the intermediate sheets 8. Referring to FIG. 5, the openings 8*a* are arranged so as not to overlap with the main body holes 4 and the lid holes 5 in plan view. Specifically, it is preferable to make an arrangement of the openings 8*a* and the main body holes 4 and the lid holes 5 so that the steam 11 would not flow straight. In other words, it is preferable not to form holes (the main body holes 4 and the lid holes 5) in the vicinity of the center of the casing 2 because the openings 8*a* are arranged in the center.

Figure 3:
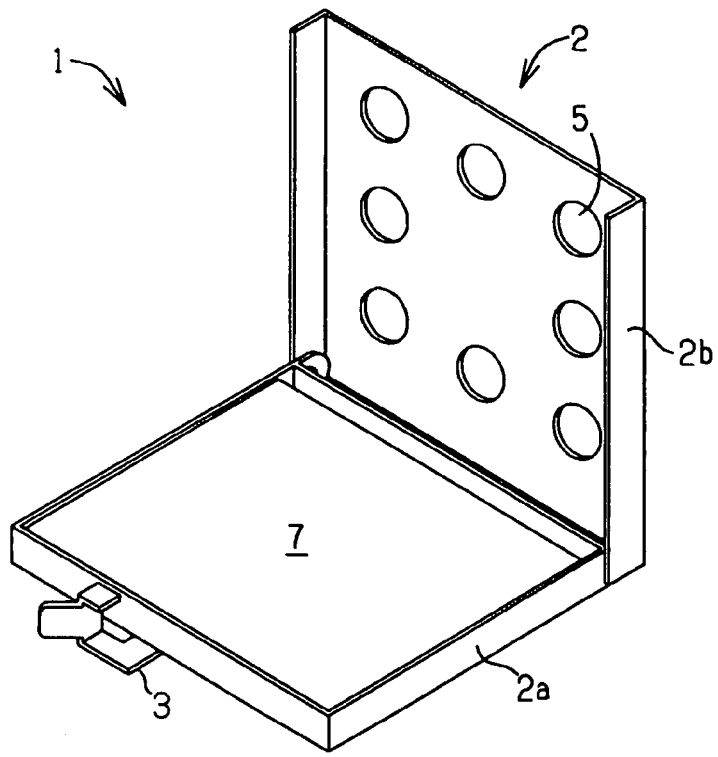
FIG. 3 is a perspective view of the challenge device in a state in which the sheets have been fitted into the casing.

Further, the entire thickness of the group 6 of sheets (the total thickness of one upper sheet 7, 16 intermediate sheets 8, and one lower sheet 9) is preferably in conformity with a height H (FIG. 1) of the casing 2 enough to house the group 6 of sheets therein. If the group 6 is thin, as shown in FIG. 3, gap is left in a thickness direction in housing the group 6 in the casing 2, and the supplied steam 11 passes through the gap, resulting in disrupting a test environment. Conversely, if the group 6 is thick, the group 6 is not accommodated in the casing 2. Consequently, it is preferable that the thickness of the group 6 is in conformity with the height H (or in substantially conformity enough to have no gap) and the sheets 7, 8, and 9 are in very close contact with one another within the casing 2.

Further, the numbers of the upper sheet(s) 7 and the lower sheet(s) 9 are arranged so that the entire thickness is in conformity with the height H as much as possible in view of the number of the intermediate sheets 8. Consequently, the example shown in FIG. 1 has one upper sheet 7 and one lower sheet 9, but may have more than one.

Herein, as shown in FIG. 1, the upper sheet 7, the intermediate sheets 8, and the lower sheet 9 each have a cutoff portion (positioner) 12 at one of its corners. Especially, the cutoff portions 12 formed at the intermediate sheets 8 facilitate adjusting or aligning directions of the openings 8*a*, thereby improving working efficiency in assembly of the challenge device 1. Through the positioners 12, alignment of the openings 8*a* in the stacked intermediate sheets 8 consistently in a predetermined manner is facilitated. Further, the cutoff portions 12 also formed at the upper and the lower sheets 7 and 9 facilitate handling the group 6 of sheets as a whole. As the positioner, it is possible to make a slit in some portion, to color one side in the same color, or to change a size (such as a size in height and width) or a shape, instead of forming the cutoff portions 12 at a corner of each sheet.

The indicator 10 may be selected at the discretion of one who is to perform an examination. Specifically, a chemical indicator, a biological indicator, or a data logger indicator may be used as the indicator 10.

A data logger indicator is designed to send data detected by a detector such as a temperature sensor to a data processor such as a computer, whereby the data is processed. It is preferable to send and receive data between the detector and the data processor via radio waves such as infrared communication. The data logger indicator is provided with a temperature sensor, a memory module, an interface (such as infrared communication) for transmitting data to a computer, and a timer, being capable of storing a temperature history of the challenge device 1. Thus, the use of the data logger indicator observes a sterilization environment (permeation rate of steam into an article to be sterilized) in real time. After a lapse of a few minutes upon starting of a test, for example, the detector obtains data every one second, which is sent to the data processor via the interface.

A chemical indicator is designed to turn its original color into a predetermined color upon completion of sterilization (exposure to a predetermined temperature history). A biological indicator is designed to be placed under an environment suitable for culturing bacteria after sterilization to check the degree of color change after a predetermined time. For example, if bacteria are still alive in spite of sterilization, the bacteria are cultured, resulting in turning color of the indicator, which is originally blue, into yellow. These indicators each have an advantage and a disadvantage, and thus examiners may use the best indicator each time.

The challenge device 1 is constituted by the above-mentioned components. Now, an assembly process of the challenge device 1 will be described in detail below.

First, as shown in FIG. 1, an indicator 10 to be used is selected and the intermediate sheets 8 having the openings 8*a* for accommodating the indicator 10 to be used are prepared.

Figure 2:
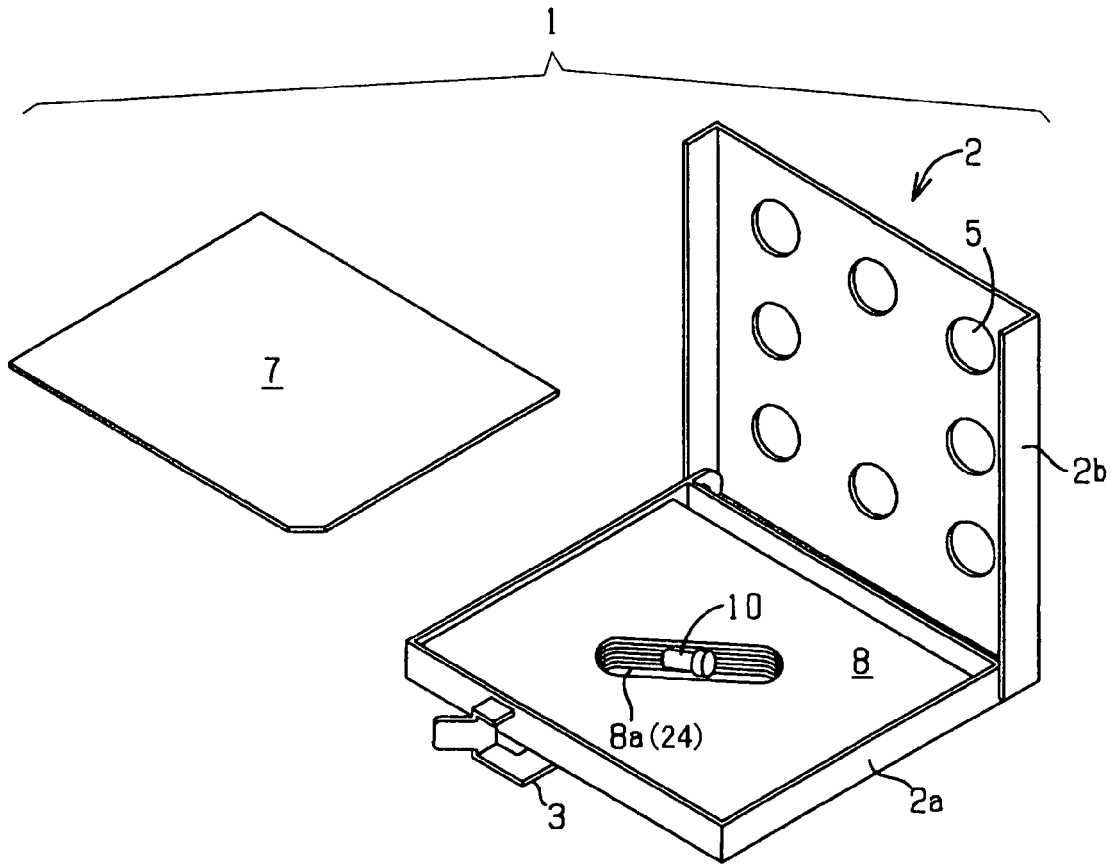
FIG. 2 is a perspective view of the challenge device in the process of fitting sheets into a casing.

Then, as shown in FIG. 2, the lower sheet 9 and the intermediate sheets 8 are fitted into the casing 2, and further, the indicator 10 is inserted into the cavity 24 formed by the openings 8*a* communicated with one another of the intermediate sheets 8. In the condition shown in FIG. 2, the bottom opening of the cavity 24 is closed by the lower sheet 9.

Next, as shown in FIG. 3, the upper sheet 7 is set in the casing 2. In the condition shown in FIG. 3, the top opening of the cavity 24 is closed by the upper sheet 7. Thus, the bottom opening and the top opening of the cavity 24 are closed, and whereby a closed cavity 14 (shown in FIG. 6 described below) is formed within the group 6 of sheets.

The indicator 10 may be contained in the closed cavity 14 of the group 6 in advance, and then the group 6 may be fitted into the casing 2.

Then, as shown in FIG. 4, when the casing 2 is closed and the latch 3 is locked, the group 6 of sheets is encased in the casing 2. Conversely, when the latch 3 is unlocked, the group 6 can be taken out of the casing 2.

As above, the assembly of the challenge device 1 is completed.

Figure 6:
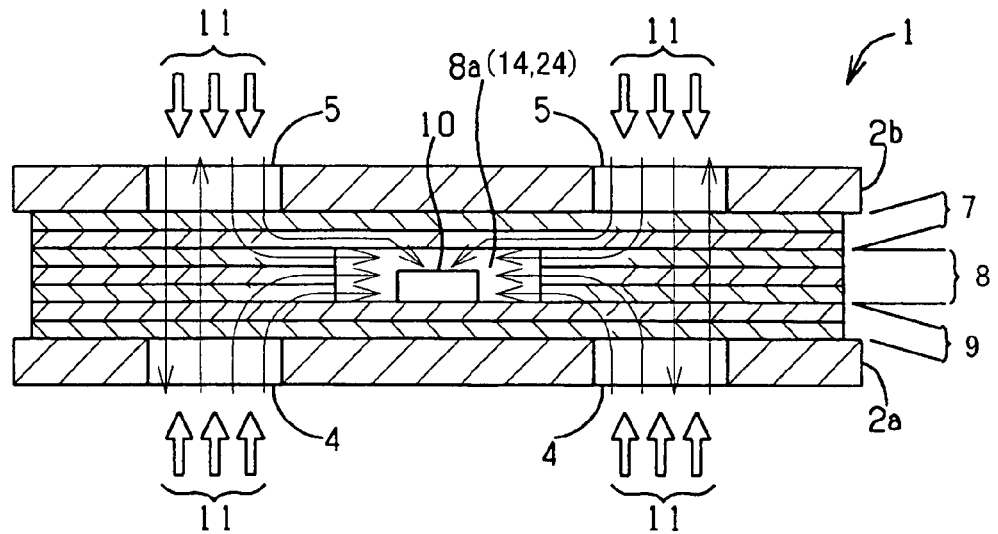
FIG. 6 is a cross section showing a state in which high-pressure steam is introduced into the challenge device.

The challenge device 1 assembled in this way is placed within a sterilization chamber not shown. FIG. 6 is a cross section showing a state in which the high-pressure steam 11 is introduced into the challenge device 1 within the sterilization chamber. As shown in FIG. 6, the closed cavity 14 is formed within the device 1 by the cavity 24, which is formed by a plurality of openings 8*a* communicated with one another, whose top opening and bottom opening are closed respectively by the upper sheet 7 and the lower sheet 9.

Within a test chamber (the sterilization chamber), the high-pressure steam 11 (hereinafter referred to as the steam 11) is supplied to the challenge device 1. The steam 11 is introduced through the main body holes 4 and the lid holes 5 into the device 1, part thereof permeating through the upper and the lower sheets 7 and 9 and the intermediate sheets 8 into the closed cavity 14. The indicator 10 in the closed cavity 14 is placed under such an environment filled with the steam 11 of high temperature and high pressure, showing a predetermined reaction based on this environment.

After sterilization, the casing 2 is opened after temperature of the device 1 has decreased, whereupon the group 6 and the indicator 10 are taken out thereof. Whether steam permeation into the article to be sterilized has been well done is judged by the indicator 10 (a chemical one or a biological one) having taken out. The group 6 is made of paper or pulp, as described above, so as to be used for a plurality of runs of examination. At this time, washing required in the conventional way using towels or gauzes is not necessary. The inventor confirmed by the experiments that about 20 to 30 runs of examination had not affected examination results without washing the group 6 of sheets.

The device 1 is placed in the sterilization chamber with articles such as medical cloth and instrument to be sterilized, so that the articles are sterilized while the device 1 monitors a sterilization environment.

Next, modified embodiments of the openings 8a formed in the intermediate sheets 8 will be described in detail, making reference to FIGS. 7 to 9C. The openings 8a shown in FIG. 1 each are formed in advance in the intermediate sheets 8, but examples shown in FIGS. 7 to 9C illustrate openings formed according to need.

Figure 7:
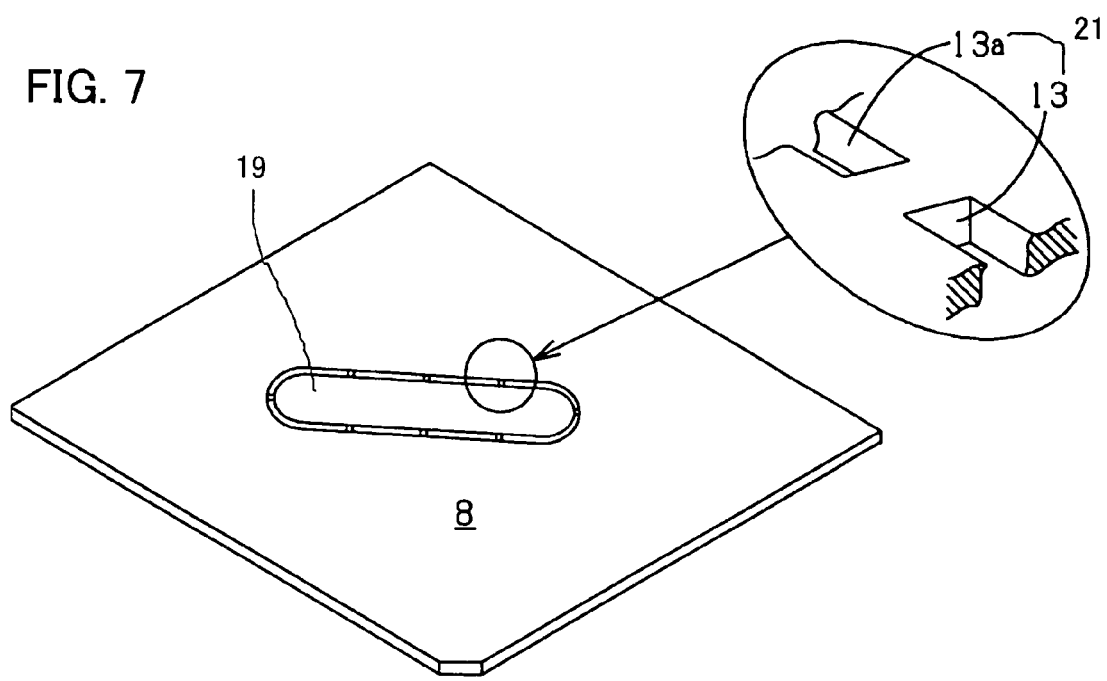
FIG. 7 is a perspective view of an intermediate sheet and an enlarged perspective view of the vicinity of an opening thereof.

FIG. 7 is a perspective view of an intermediate sheet 8 and an enlarged perspective view of the vicinity of an opening 8a thereof. FIGS. 8A to 8F and 9A to 9C are enlarged plan views of the vicinities of openings 8b and 8c of intermediate sheets 8, respectively. As shown in FIGS. 7 to 9C, the intermediate sheets 8 each have a portion 19 removable by being broken in advance.

The opening 8a shown in the example in FIG. 7 is an elongated hole similar to the opening 8a of the intermediate sheet 8 in FIG. 1, but it is not until the removable portion 19 is broken and removed that the opening 8a is formed in the intermediate sheet 8 in FIG. 7. Specifically, the removable portion 19 is entirely surrounded by a breakable line 21. The breakable line 21 consists of intermittent slots 13a and bridge-like breakable portions 13 each formed between two of the slots 13a. The opening 8a is formed in each sheet 8 by breaking the breakable portions 13 and removing the removable portion 19. The openings 8a can be formed in required number of intermediate sheets 8. The intermediate sheets 8 whose breakable portions 13 are not broken can be used, for example, as the upper sheet 7 or the lower sheet 9.

Figure 8A:
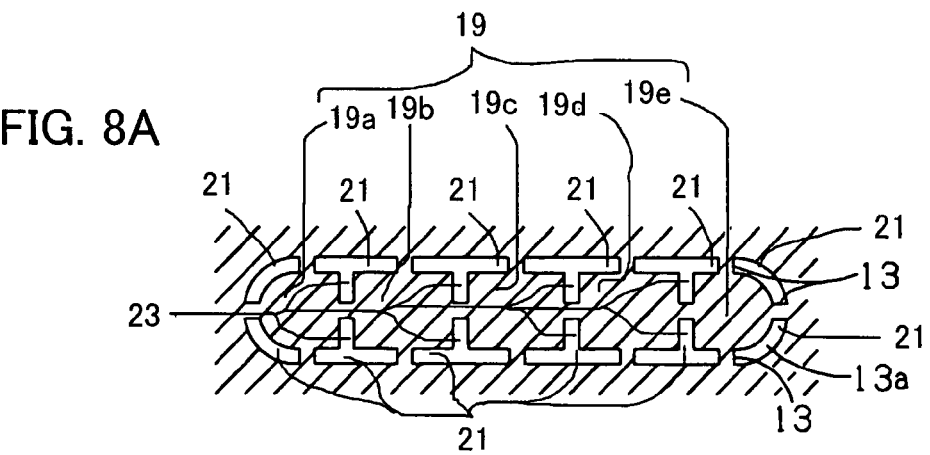
FIGS. 8A to 8F each are an enlarged plan view of the vicinity of an opening of an intermediate sheet.

FIGS. 8A to 8F show examples in which the size of the opening 8b is adjustable. FIGS. 8A to 8F are not cross sections, but only cut portions (slots 13a) of the sheets are illustrated by outlines, and portions where the sheets exist are hatched. Specifically, as shown in FIG. 8A, the breakable portions 13 and the intermittent slots 13a are arranged so as to form the opening 8b according to need as shown in FIGS. 8B to 8F.

More specifically, a removable portion 19 is composed of a plurality of blocks 19a to 19e. The portion 19 is entirely surrounded by a breakable line 21 and further has rib-like breakable lines 23 each between the blocks 19a to 19e, the breakable lines 21 and 23 being like a ladder as a whole. The breakable lines 21 and 23 consist of intermittent slots 13a and bridge-like breakable portions 13 each formed between two of the slots 13a. The opening 8b is formed in each sheet 8 by breaking the breakable portion 13 and removing any block. The desired area, shape, and number of openings 8b can be formed by removal of the discretional number of blocks.

Figure 8B:
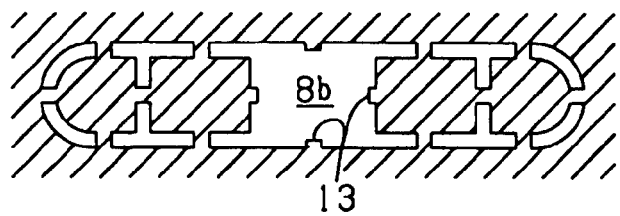
Figure 8C:
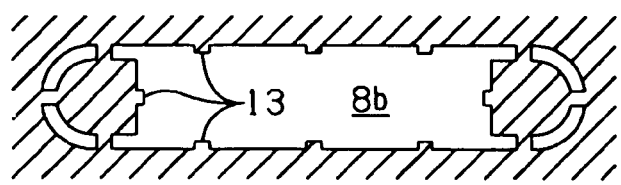
Figure 8D:
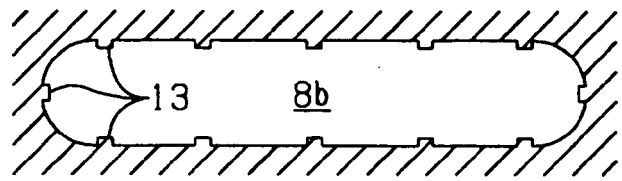
Figure 8E:
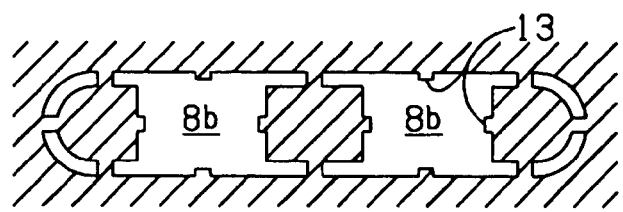
Figure 8F:
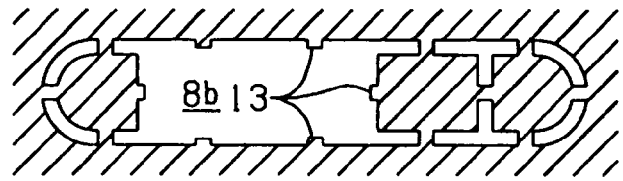

In the example shown in FIG. 8B, the smallest opening 8b is formed, whereas in the example shown in FIG. 8D, the largest opening 8b is formed. In the example shown in FIG. 8C, the opening 8b is substantially intermediate in size between the openings 8b shown in FIGS. 8B and 8D. In the example shown in FIG. 8E, two openings 8b are formed. Further, as shown in FIG. 8F, the openings 8b of an asymmetrical shape can be formed. Various formation of the opening 8b can be considered other than the above-mentioned examples, and the opening 8b can be formed at discretion by breaking the portion 13 in response to a shape, a size, or the number of the indicator 10 to be used.

Figure 9A:
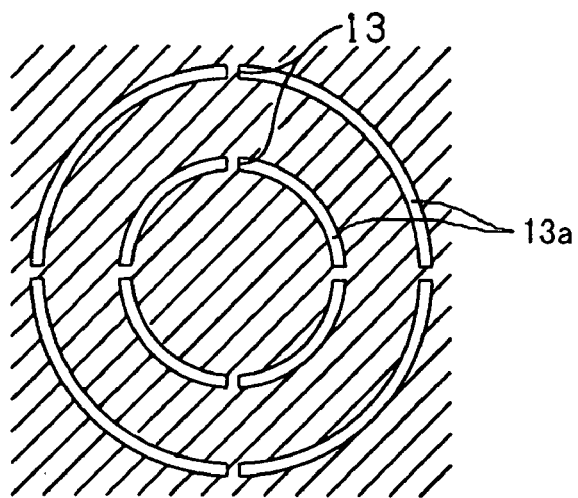
FIGS. 9A to 9C each are an enlarged plan view of the vicinity of an opening of an intermediate sheet, which opening has a different shape from those in FIGS. 7 to 8F.
Figure 9B:
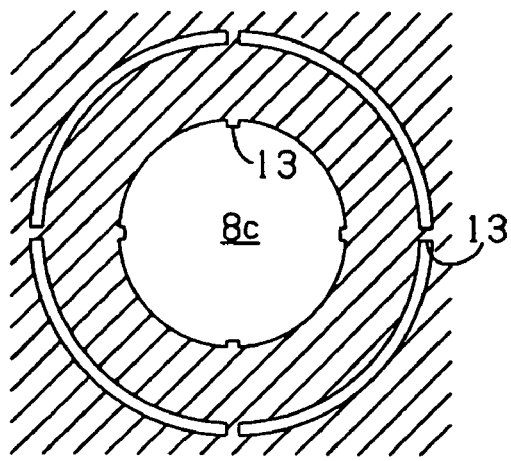
Figure 9C:
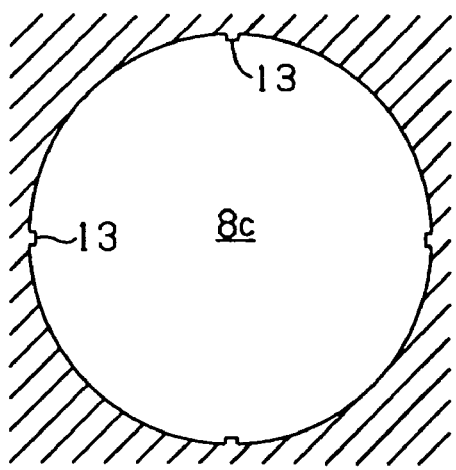

Provision of breakable lines in a concentric fashion responds to a length in a width direction of an indicator 10 by breaking any circular part. FIGS. 9A to 9C show examples in which the opening 8c is formed in a concentric fashion. In the example shown in FIG. 9B, the small opening 8c is formed, whereas in the example shown in FIG. 9C, the large opening 8c is formed.

An opening can be of a shape other than those shown in the examples only if the opening accommodates the indicator 10 and a desired examination environment is obtainable. Further, the openings can be the same shape or take a relative displacement in plan view.

Figure 10:
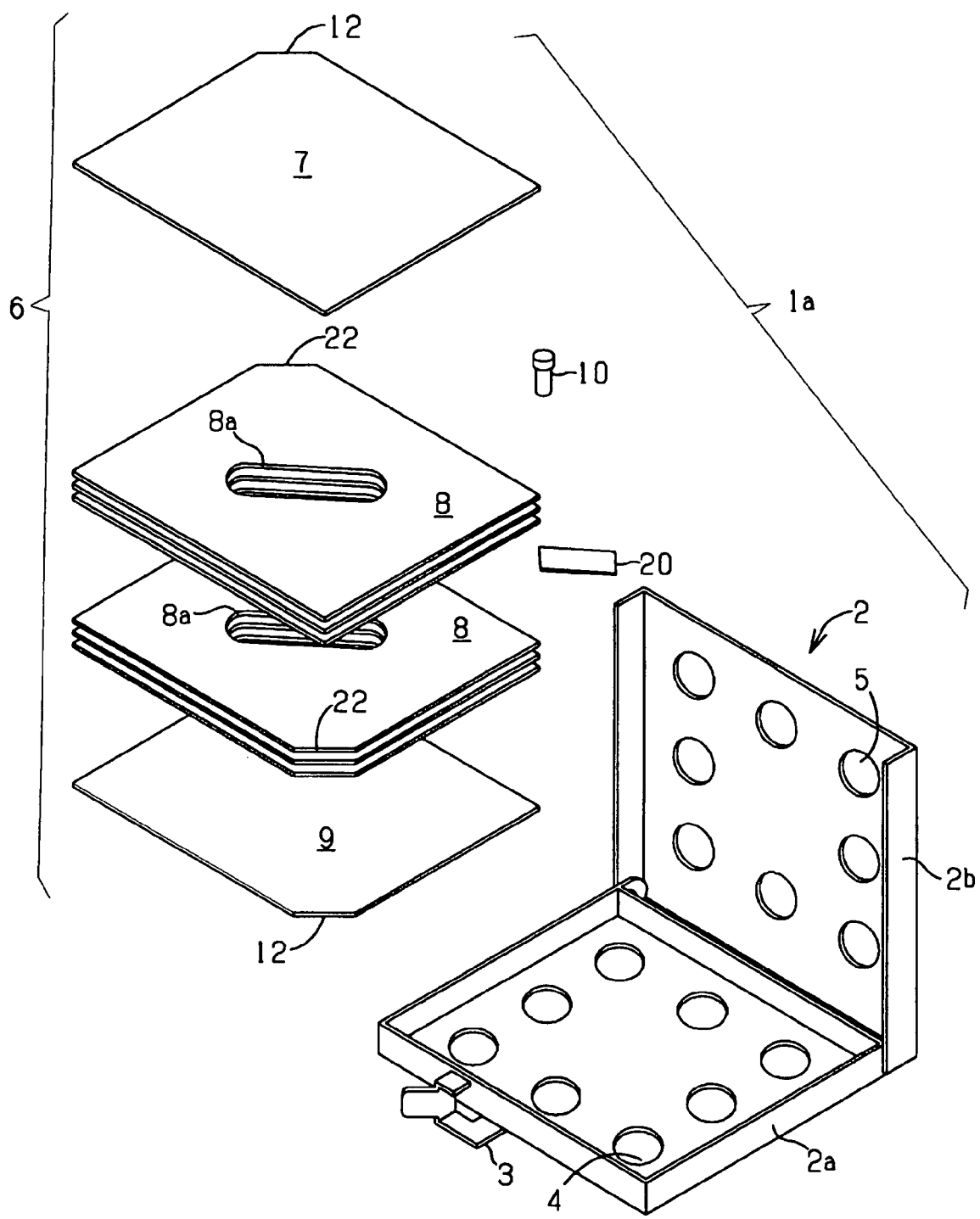
FIG. 10 is an exploded perspective view of a modified embodiment of the challenge device in FIG. 1.
Figure 11:
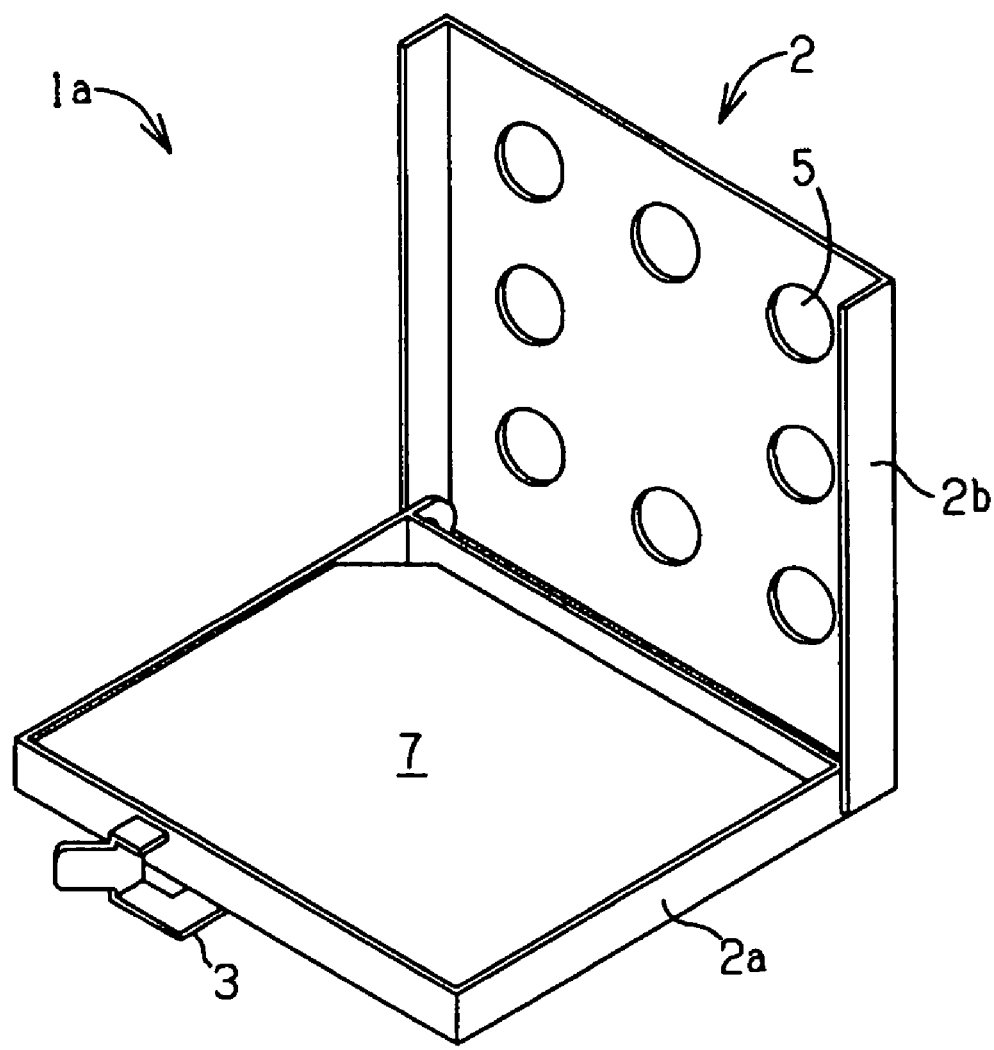
FIG. 11 is a perspective view of the challenge device in FIG. 10 in a state in which sheets and an indicator is set in a casing.

Modified challenge devices for a high-pressure steam sterilizer embodying the present invention will be described in detail below, making reference to FIGS. 10 to 14B. FIG. 10 is an exploded perspective view of a modified embodiment of the challenge device in FIG. 1. FIG. 11 is a perspective view of the challenge device of the modified embodiment shown in FIG. 10 in a state in which sheets and an indicator is set in a casing.

A challenge device 1a shown in FIG. 10 is different from the challenge device 1 shown in FIG. 1 in that a chemical indicator 20 of a shape of a sheet is slipped in between a plurality of intermediate sheets 8. The chemical indicator 20 is interposed between two pieces of the intermediate sheets 8 at a portion where openings 8a are not formed, so as to be placed within the intermediate sheets 8.

At this time, it is preferable to slip the indicator 20 in between the $8^{th}$ and the $9^{th}$ sheets among 16 intermediate sheets 8 (only six sheets among them are illustrated in FIG. 10). Thus, as shown in FIG. 10, the $1^{st}$ through $8^{th}$ intermediate sheets 8 from the bottom are arranged so that their cutoff portions 22 come to the near side of the figure, whereas the $9^{th}$ through $16^{th}$ intermediate sheets 8 from the bottom are arranged so that their cutoff portions 22 come to the far side of the figure. Such arrangements orient the elongated openings 8a in the same direction, and further, define the boundary between the $8^{th}$ and the $9^{th}$ intermediate sheets 8 where the indicator 20 is set. That facilitates collecting the indicator 20 after examination.

Further, such an arrangement that cutoff portions 12 of the lower sheet 9 and the upper sheet 7 are arranged at the same position as the cutoff portions 22 of the respective adjacent intermediate sheets 8 remarkably facilitates handling of a group 6 of sheets composed of the lower sheet 9, the intermediate sheets 8, and the upper sheet 7.

The group 6 composed of the lower sheet 9, the intermediate sheets 8, and the upper sheet 7 are fitted into a casing 2, as shown in FIG. 11, and thereafter a lid 2b is closed, so that the challenge device 1a is put under the same configuration as the challenge device 1 shown in FIG. 4.

Figure 12A:
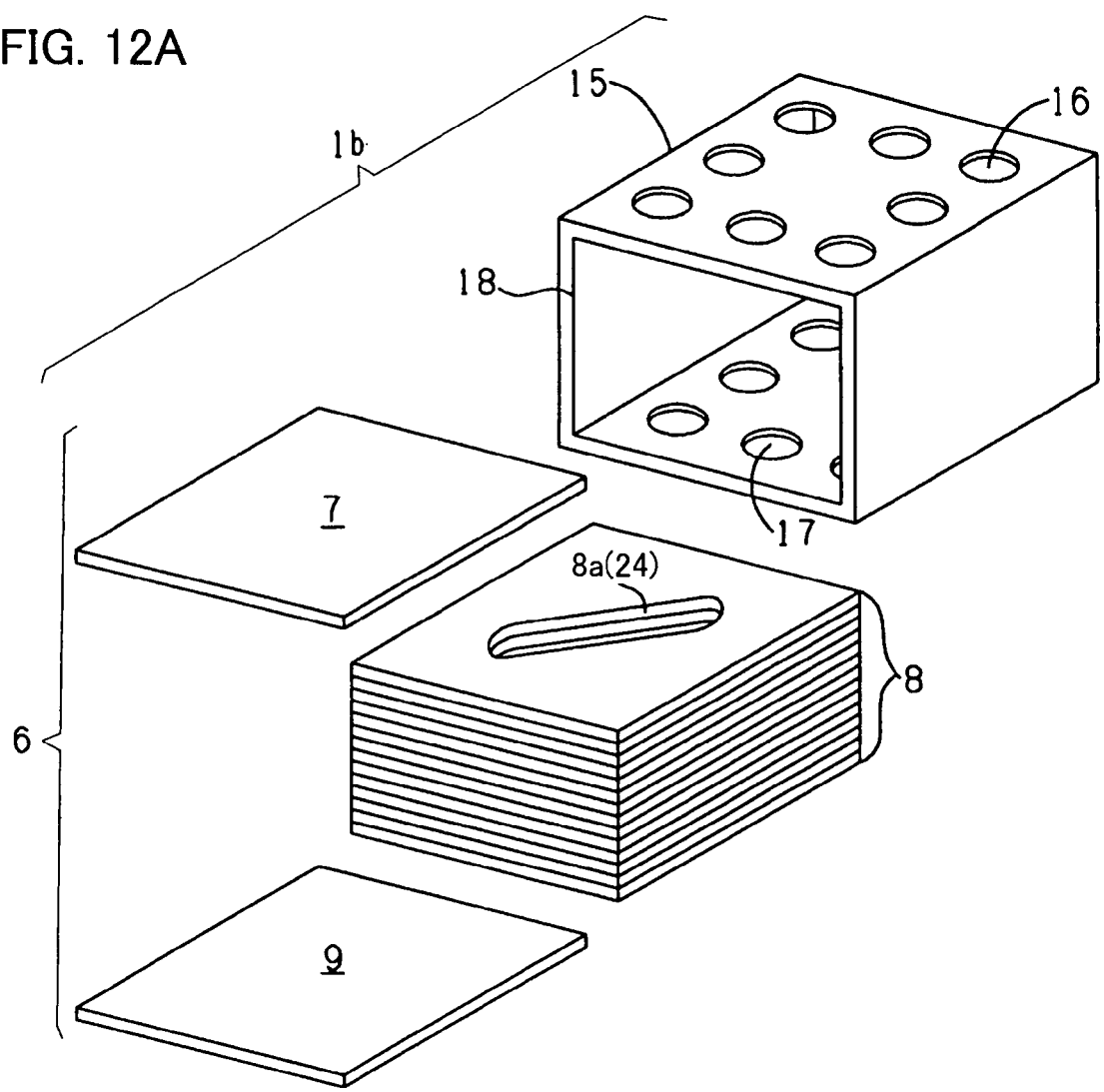
FIGS. 12A and 12B are perspective views of a challenge device for a high-pressure steam sterilizer, FIG. 12A showing a state before sheets are fitted into a casing different from the casing shown in FIG. 1, FIG. 12B showing a state containing the sheets in the casing.
Figure 12B:
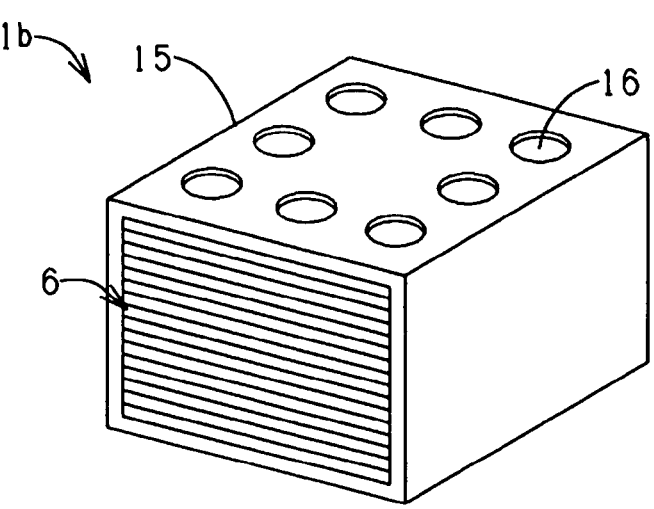

Next, an example in which the group 6 is contained in a casing 15 having another configuration will be described in detail, making reference to FIGS. 12A and 12B. FIG. 12A is a perspective view of a challenge device 1b for a high-pressure steam sterilizer in a state before the sheets are fitted into the casing 15 different from the casing 2 shown in FIG. 1. FIG. 12B is a perspective view of the challenge device 1b in a state containing the sheets in the casing 15.

As shown in FIG. 12A, the casing 15 has at top and bottom walls holes 16 and 17 so as to pass steam therethrough, respectively. Though not illustrated, a face of the casing 15 on the far side of the figure may have a wall or not. Specifically, only a face on the near side of the figure may have an opening 18, or the both faces may be open. The above-mentioned stacked group 6 of sheets is inserted into the casing 15 through such the opening 18, so that the challenge device 1b is put under a state shown in FIG. 12B.

Figure 13A:
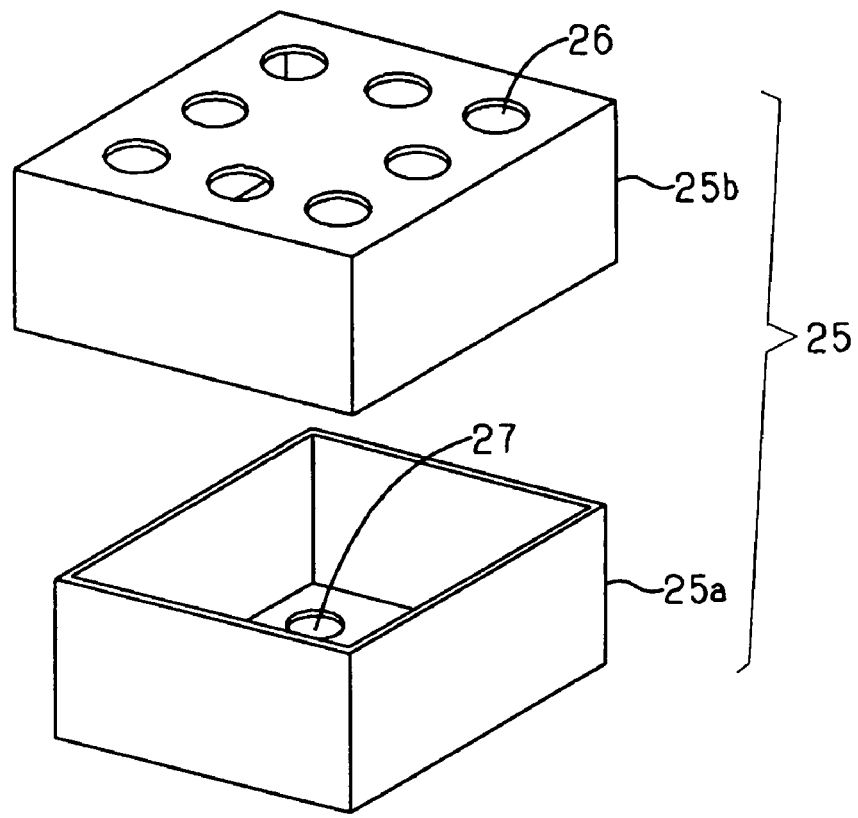
FIG. 13A is a perspective view of a main body and a lid of a casing usable in a further embodiment of the present invention.
Figure 13B:
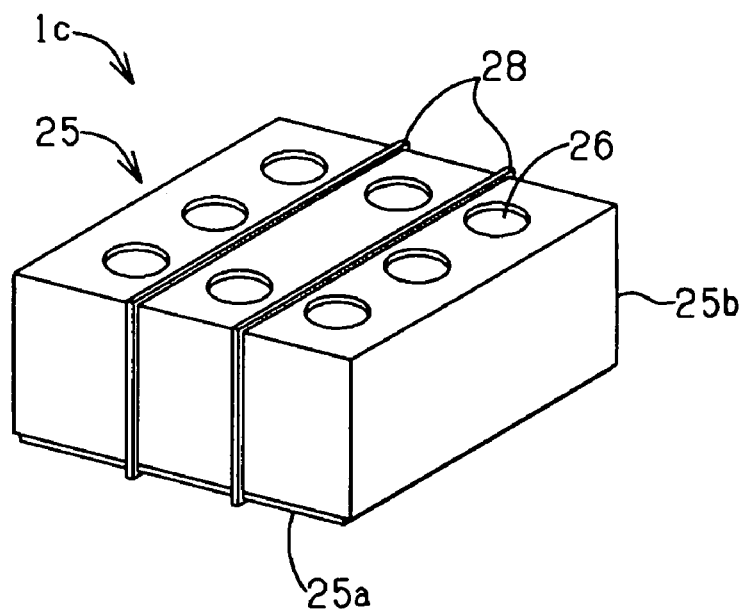
FIG. 13B is a perspective view of a challenge device for a high-pressure steam sterilizer in a state after assembly of the main body and the lid in FIG. 13A.

Next, an example employing a casing 25 having a shape different from any of the above-mentioned ones will be illustrated in FIGS. 13A and 13B. FIG. 13A is a perspective view of a main body and a lid of a casing usable in a further embodiment of the present invention. FIG. 13B is a perspective view of a challenge device 1c for a high-pressure steam sterilizer in a state after assembly of the main body and the lid in FIG. 13A.

As shown in FIG. 13A, the casing 25 mainly consists of a main body 25a whose top face is open and a lid 25b whose bottom face is open. The main body 25a and the lid 25b each are made of a steam-impermeable material, the top face (upper wall) of the lid 25b having a plurality of holes 26 so as to pass steam therethrough, and the bottom face (bottom wall) of the main body 25a also having a plurality of holes 27 so as to pass steam therethrough.

The group 6 of sheets described above, not shown in FIG. 13A, is fitted into the main body 25a, which is then covered by the lid 25b, and further, as shown in FIG. 13B, the main body 25a and the lid 25b are bound together by a string (holder or binder) 28 so as to unite them. Binding by the string 28 applies appropriate pressing force on the group 6 (not shown) within the casing 25, thereby performing excellent examinations for a high-pressure steam sterilization. The string 28 is preferably made of a stretch material, and may be a rubber band.

Figure 14A:
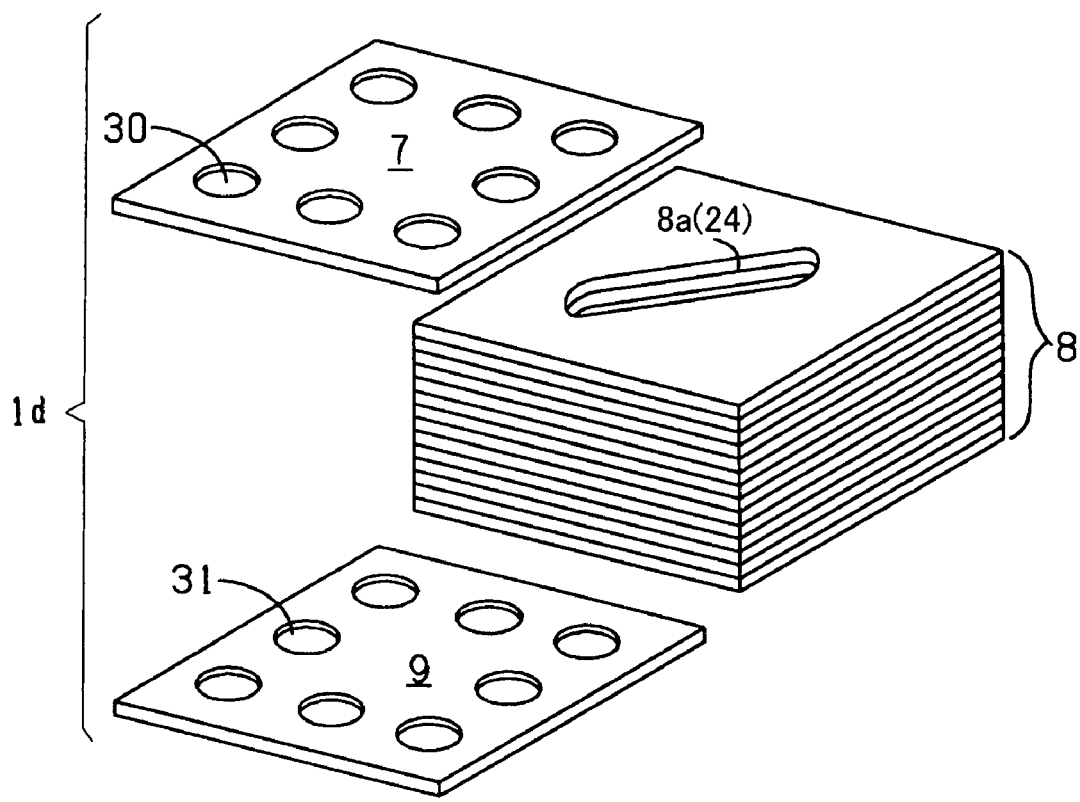
FIGS. 14A and 14B are perspective views of a further modified challenge device for a high-pressure steam sterilizer of the present invention, FIG. 14A showing a state before assembly, FIG. 14B showing a state after assembly.
Figure 14B:
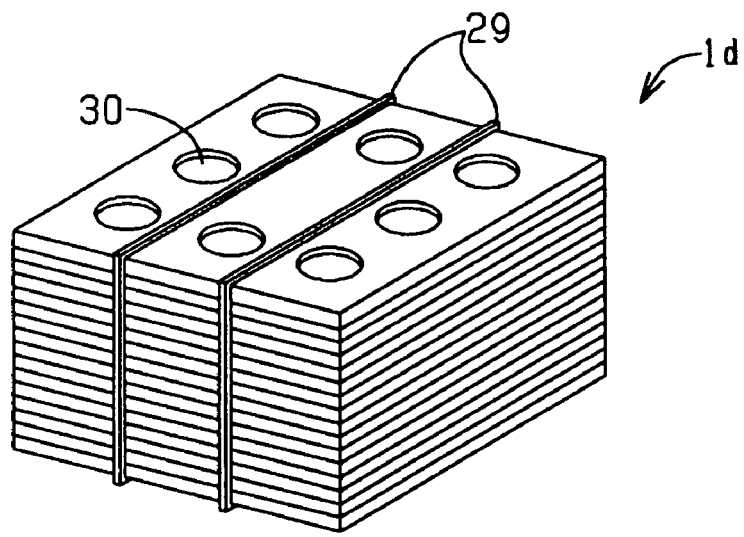

In the examples illustrated above, the group 6 of sheets is contained in the casing 2, 15, or 25, but it is possible to achieve sterilization effect by directly binding the group 6 by a binder (holder) such as a tape or a string. Such an example will be described below, making reference to FIGS. 14A and 14B. FIG. 14A is a perspective view before assembly of a further modified challenge device 1d for a high-pressure steam sterilizer of the present invention. FIG. 14B is a perspective view after assembly of the challenge device 1d shown in FIG. 14A.

As shown in FIG. 14A, the device 1d includes no casing. An upper sheet 7 and a lower sheet 9 each are made of a rigid material, and a plurality of intermediate sheets 8 are arranged therebetween. The upper sheet 7 has holes 30 so as to pass steam therethrough, and similarly, the lower sheet 9 has holes 31 so as to pass steam therethrough. The upper sheet 7 and the lower sheet 9 interpose the intermediate sheets 8 therebetween from top and bottom, and further, as shown in FIG. 14B, a stretch string 29 unites the sheets 7, 8, 9.

FIG. 14A illustrates the example in which separate sheets are stacked, but one side of the group 6 (the lower sheet 9, the intermediate sheets 8, and the upper sheet 7) can be fastened like a book. Specifically, there is no compelling reason to make the upper sheet 7, the intermediate sheets 8, and the lower sheet 9 to be separate, and for example, it is possible that one side of the sheets is fastened in advance and the other side is fixed by a binder such as a string or a holder such as the latch 3 as shown in FIG. 1 so as not to be open after insertion of the indicator into the closed cavity 14 formed by the openings 8a of the intermediate sheets 8 communicated with one another.

The challenge device 1 of the present invention as constituted as above obtained the substantially equivalent sterilization environment in the case of employing either indicator of a chemical indicator, a data logger indicator, or a biological indicator as the indicator 10, as a result of sterilizing examination under the same sterilization environment as that of a process challenge device (constructed by folded towels) in the AAMI standard in the United States.

Consequently, the challenge device embodying the present invention has the same level of air-discharge and steam permeable load as those of a process challenge device in the AAMI standard.

The invention claimed is:

1. A process challenge device for a high-pressure steam sterilizer, comprising:
   a plurality of steam permeable bodies formed by a steam permeable material;
   an indicator changeable in appearance on exposure to a predetermined temperature history; and
   a holder,
   wherein the steam permeable bodies comprise at least one end steam permeable body and a plurality of intermediate steam permeable bodies,
   wherein the steam permeable bodies are stacked with the end steam permeable body arranged at at least one end,
   the intermediate steam permeable bodies each having an opening,
   the openings of the intermediate steam permeable bodies being communicated with one another to form a cavity,
   the cavity being closed at at least one end by the end steam permeable body, the indicator being contained in the cavity, and
   wherein the holder holds the stacked steam permeable bodies having therein the indicator in a stacked fashion,
   wherein the holder has a plurality of discrete holes therethrough strategically located with respect to the steam permeable bodies to controllably pass steam to the steam permeable bodies,
   wherein the intermediate steam permable bodies each has a positioner, whereby a direction of the intermediate steam permable bodies is adjusted in being stacked to thereby facilitate alignment of the openings in the intermediate steam permable bodies consistently in a predetermined manner.

2. The process challenge device as defined in claim 1, wherein the steam permeable bodies each are of a shape of a sheet.

3. The process challenge device as defined in claim 1, wherein the steam permeable bodies have at least two end steam permeable bodies, so as to be stacked with the end steam permeable bodies arranged at both ends thereof, and
   the cavity being closed at both sides by the end steam permeable bodies.

4. The process challenge device as defined in claim 1, wherein the holder is a casing, and
   wherein the stacked steam permeable bodies are set into the casing, so as to be held in a stacked fashion.

5. The process challenge device as defined in claim 4, the casing comprising a main body and a lid and being lockable with the lid closed.

6. The process challenge device as defined in claim 5, wherein the plurality of discrete holes comprises a first plurality of discrete holes in the main body and a second plurality of discrete holes in the lid.

7. The process challenge device as defined in claim 6, wherein discrete holes in the first plurality of discrete holes align with discrete holes in the second plurality of discrete holes with the lid closed on the main body.

8. The process challenge device as defined in claim 1, the holes having a total area of 3 to 30% of the overall area of a surface where the holes are formed.

9. The process challenge device as defined in claim 8, wherein the holder is a casing comprising a main body and a lid and the surface having the holes is on the lid.

10. The process challenge device as defined in claim 8, wherein the steam permeable bodies comprise at least one of: a) cotton or glass fiber compressed in a unified manner; b) heat-resisting nonwoven fabric; c) paper; d) cork; and e) pulp.

11. The process challenge device as defined in claim 8 wherein the holes have a total area of 5-20% of the overall area of a surface where the holes are formed.

12. The process challenge device as defined in claim 8 wherein the holes have a total area of 8-12% of the overall area of a surface where the holes are formed.

13. The process challenge device as defined in claim 1, wherein the holder is a binder, and
wherein the stacked steam permeable bodies are bound by the binder, so as to be held in a stacked fashion.

14. The process challenge device as defined in claim 1, wherein the indicator is one selected from a group consisting of a chemical indicator, a biological indicator and a data logger indicator.

15. The process challenge device as defined in claim 1, wherein the holder is made from one of: a) a high-pressure steam resistant material; and b) a material that has a lower steam permeability than a steam permeability of the plurality of steam permeable bodies.

16. The process challenge device as defined in claim 1, wherein the discrete holes do not align with the openings of the intermediate steam permeable bodies.

17. The process challenge device as defined in claim 1, wherein the at least one end steam permeable body has a positioner for adjusting a direction of the at least one end steam permeable body relative to the intermediate steam permeable bodies.

18. The process challenge device as defined in claim 1, wherein each of the positioners comprises a cutoff portion.

19. The process challenge device as defined in claim 1, wherein the holder is made from a high-pressure steam resistant material.

20. A process challenge device for a high-pressure steam sterilizer, comprising:
a plurality of steam permeable bodies formed by a steam permeable material; and
a holder,
wherein the steam permeable bodies comprise at least one end steam permeable body and a plurality of intermediate steam permeable bodies, the intermediate steam permeable bodies each having an opening,
the openings of the intermediate steam permeable bodies being adapted to be communicated with one another by stacking of the steam permeable bodies with the end steam permeable body arranged at the end, so as to form a cavity closed at at least one end by the end steam permeable body,
the cavity being designed to contain an indicator changeable in appearance on exposure to a predetermined temperature history, and
wherein the holder is adapted to hold the stacked steam permeable bodies in a stacked fashion,
wherein the holder has a plurality of discrete holes therethrough strategically located with respect to the steam permeable bodies to controllably pass steam to the steam permeable bodies,
wherein the intermediate steam permeable bodies each has a positioner, whereby a direction of the intermediate steam permeable bodies is adjusted in being stacked to thereby facilitate alignment of the openings in the intermediate steam permeable bodies consistently in a predetermined manner.

21. The process challenge device as defined in claim 20, further comprising an indicator to be contained in the cavity.

22. The process challenge device as defined in claim 21, wherein the indicator is one selected from a group consisting of a chemical indicator, a biological indicator and a data logger indicator.

23. The process challenge device as defined in claim 20, wherein the steam permeable bodies each are of a shape of a sheet.

24. The process challenge device as defined in claim 20, wherein the steam permeable bodies all have the same outer shape.

25. The process challenge device as defined in claim 20, wherein the at least one end steam permeable body has a positioner for adjusting a direction of the at least one end steam permeable body relative to the intermediate steam permeable bodies.

26. The process challenge device as defined in claim 20, wherein the steam permeable bodies are stacked and fixed to one another at one side.

27. The process challenge device as defined in claim 20, wherein the holder is a casing comprising a main body and a lid,
where the plurality of discrete holes comprises a first plurality of discrete holes in the main body and a second plurality of discrete holes in the lid.

28. The process challenge device as defined in claim 20, wherein each of the positioners comprises a cutoff portion.

29. The process challenge device as defined in claim 20, wherein the discrete holes in the holder have a total area of 3 to 30% of the overall area of a surface where the holes are formed and the steam permeable bodies comprise at least one of: a) cotton or glass fiber compressed in a unified manner; b) heat-resisting nonwoven fabric; c) paper; d) cork; and e) pulp.

30. The process challenge device as defined in claim 20, wherein the holder is made from a high-pressure steam resistant material.

31. The process challenge device as defined in claim 20 wherein the discrete holes extend around the cavity.

32. The process challenge device as defined in claim 31 wherein the discrete holes are spaced, at substantially like intervals, each from adjacent discrete holes.

33. The process challenge device as defined in claim 32 wherein the holes surround the cavity.

34. A process challenge device for a high-pressure steam sterilizer, comprising:
a plurality of steam permeable bodies formed by a steam permeable material; and
a holder,
wherein the steam permeable bodies comprise at least one end steam permeable body and a plurality of intermediate steam permeable bodies, the intermediate steam permeable bodies each having a removable portion, so as to form an opening by removing the portion,
the openings of the intermediate steam permeable bodies being adapted to be communicated with one another by stacking of the intermediate steam permeable bodies in which the openings are formed and the end steam permeable body arranged at the end, so as to form a cavity closed at its end by the end steam permeable bodies,
the cavity being designed to contain an indicator changeable in appearance on exposure to a predetermined temperature history, and
wherein the holder is adapted to hold the stacked steam permeable bodies in a stacked fashion, wherein the holder has a plurality of discrete holes therethrough strategically located with respect to the steam permeable bodies to controllably pass steam to the steam permeable bodies, wherein the intermediate steam permeable bodies each has a positioner, whereby a direction of the intermediate steam permeable bodies is adjusted in being stacked to thereby facilitate alignment of the openings in the intermediate steam permeable bodies consistently in a predetermined manner.

35. The process challenge device as defined in claim 34, wherein the holder is a casing comprising a main body and a lid, where the plurality of discrete holes comprises a first plurality of discrete holes in the main body and a second plurality of discrete holes in the lid.

36. The process challenge device as defined in claim 34, wherein the at least one end steam permeable body has a positioner for adjusting a direction of the at least one end steam permeable body relative to the intermediate steam permeable bodies.

37. The process challenge device as defined in claim 34, wherein each of the positioners comprises a cutoff portion.

38. The process challenge device as defined in claim 34, wherein the discrete holes in the holder have a total area of 3 to 30% of the overall area of a surface where the holes are formed and the steam permeable bodies comprise at least one of: a) cotton or glass fiber compressed in a unified manner; b) heat-resisting nonwoven fabric; c) paper; d) cork; and e) pulp.

39. The process challenge device as defined in claim 34, wherein the holder is made from a high-pressure steam resistant material.

40. The process challenge device as defined in claim 39, wherein the high-pressure steam resistant material is metal.

\* \* \* \* \*